United States Patent [19]

Koch

[11] Patent Number: 4,622,010
[45] Date of Patent: Nov. 11, 1986

[54] ENOSSAL IMPLANT FOR SECURING A TIGHT-FITTING TOOTH REPLACEMENT

[75] Inventor: Werner L. Koch, Liebenau, Fed. Rep. of Germany

[73] Assignee: Implanto-Lock GmbH, Fed. Rep. of Germany

[21] Appl. No.: 647,107

[22] Filed: Nov. 16, 1984

[30] Foreign Application Priority Data

Sep. 17, 1984 [DE] Fed. Rep. of Germany ....... 3331868

[51] Int. Cl.$^4$ ............................................. A61C 8/00
[52] U.S. Cl. .................................................. 433/173
[58] Field of Search ................ 433/173, 174, 175, 176

[56] References Cited

U.S. PATENT DOCUMENTS 4,270,905 6/1981 Mohammed ...................... 433/173
4,416,629 11/1983 Mozsary et al. ................... 433/173

*Primary Examiner*—Robert Peshock
*Attorney, Agent, or Firm*—Allegretti, Newitt, Witcoff & McAndrews, Ltd.

[57] ABSTRACT

An enossal tooth implant for a tooth replacement comprising an internally threaded metal tube for insertion into the jawbone, a rigid insert that screws into the tube containing a pin on which the tooth is mounted, and a resilient plastic cushioning sleeve between the pin and rigid insert.

12 Claims, 3 Drawing Figures

ENOSSAL IMPLANT FOR SECURING A TIGHT-FITTING TOOTH REPLACEMENT

The invention concerns an enossal implant for holding a tight-fitting tooth replacement, the pats of which fit without voids in which bacteria can lodge and ultimately give rise to infection.

An enossel implant of this type is disclosed in German patent specification No. 24 13 883, in which an externally-threaded liner made of a resilient material can be replaced by screwing into the threaded bore of the part of the implant which is inserted into the jawbone. That part has a threaded bore, into which is screwed a threaded peg which holds the tight-fitting replacement. But the mating parts are not in firm contact. The tooth-holding mechanism of a natural tooth is intended to be imitated by this resilient intermediary sleeve in the form of a threaded liner. Through the cooperating threads, the replacement and adjustment of the resilient threaded liner is possible.

The known implant fully and completely fulfills the demands for the imitation of the tooth-holding mechanism and adjustability. However, it has proven that the threaded surfaces of the liner can lead to infections. The reason for this is that the resilient material of the threaded liner is subjected to aging, whereupon the fitting forces decline, cracks form in which bacteria can lodge or gain a foothold, and this can lead in turn to inflammations.

This is accompanied by the disadvantage of the decreasing stability of the threads, and consequently, the change of the mechanical values which are being imitated. For this reason, it is necessary to replace the threaded liner at intervals of approximately a half-year. This is not only disadvantageous to the patient, but is also expensive to treat, and furthermore entails the disadvantage that, because of the frequency of replacement, damage occurs to the parts which are screwed together, which from the very beginning lack the tightness necessary to preclude bacteria.

A further development of this implant is known in which, to avoid these disadvantages, a spacer casing of metal is positioned with precision fitting with the column which is to be inserted into the jawbone. This spacer casing replaces the threaded part described and has the threaded liner of resilient material, which is critical to the formation of bacteria, in an area spaced from the jawbone or the flesh, so that the danger of inflammation is thereby reduced. Infection is not, however, absolutely excluded. The disadvantages caused by the aging of the resilient material of the threaded liner still exist; namely, the reduction of the forces between the threads, crack formation, the change of the mechanical values imitated, the need for placement at shorter intervals, and damage of the parts during replacement.

The object of the invention is to create an enossal implant of the type under discussion, in which the disadvantages of the known implant are avoided, and in which no bacterial colonies can therefore form or inflammations arise, in which no loosening occurs, and in which, especially, the time intervals for replacement are lengthened.

The object is accomplished by the structure described below and set forth in the claims.

The invention is based on the idea that the fundamental disadvantages of the known implant are caused by the fact that the resilient material itself serves for threaded holding and that as a result, the threaded connection is impaired during the aging of the resilient material. As a result, the formation of cracks and bacteria is possible. The invention thus provides a solution in which the intermediary sleeve of resilient material is firmly positioned, for example, through cementing or casting, between two parts which do not consist of this material, so that the connecting surfaces are generally not subjected to stress by screwing forces and a deflection of the material can thus not lead to a reduction of the tightness and solidity.

In order to be able, in the known manner, to adjust the mechanical values of the tooth holding mechanism which is imitated by the resilient intermediary sleeve, and to make possible the healing of the implant without the other part of the column, which, in its final position, projects out above the gums, threads are provided in the implant and specified by the invention; however, the threads are placed between parts which do not consist of resilient material (metal, for example), so that the threaded joint is completely durable. The threaded surfaces can, in the critical area, simply lie closely above or in the area of the gum, since the fitting surfaces between the threaded parts can be so precisely connected simply, for example, through turning, that a tightness is achieved which makes the penetration of bacteria impossible.

By firmly connecting the intermediary sleeve with the devices that hold the tooth replacement, on the one hand, with the other part of the column on the other hand (as for example, by cementinng or casting) the advantages of the invention are achieved. The formation of cracks, and therefore infections, are effectively excluded by this close connection.

In order to avoid excessive stressing of the bonding points between the resilient material of the intermediary sleeve of the adjacent parts, it is preferable that the extension of the mounting which holds the tooth replacement be resiliently supported. The intermediary sleeve provides this cushion in the interspace and supports the mounting for the tooth so that the bonding surfaces are stressed as little as possible. The extension for the tooth mounting is a cylindrical peg which fits in a bore in the column.

A particularly suitable further development of the invention consists of the lower part of the peg being formed as an expansible screw. This provides security against loosening, especially through moderate torison forces or rotating motions. The expansible screw can be formed very simply as a cylindrical shaft, which, through a close fit, screws into a bore in the column. This narrow, form-locking mounting avoids movements of the peg parts into each other, and also excludes the formation of minute spaces into which bacteria can penetrate.

In the cylindrical construction of the shaft of the expansible screw, the forces necessary to hold this part of the peg in the other part are slight. A slender threaded peg at the end of the expansible screw, which is also thinner in diameter, accordingly suffices for a secure connection.

Further details and advantages of the invention will be disclosed in connection with the drawing in which FIG. 1 is a cross-section through an enossal implant constructed in accordance with the invention;

Figure 1:
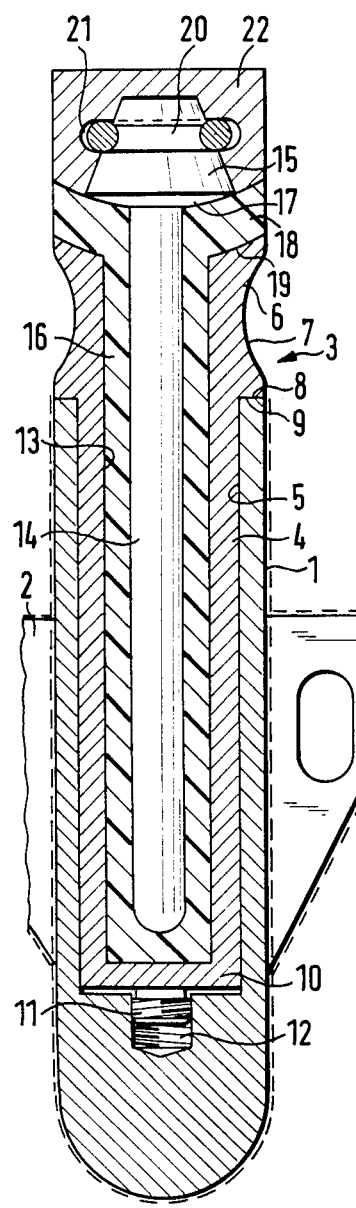
Figure 3:
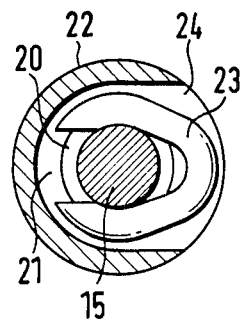
FIG. 3 is a section III—III through FIG. 2.
Figure 2:
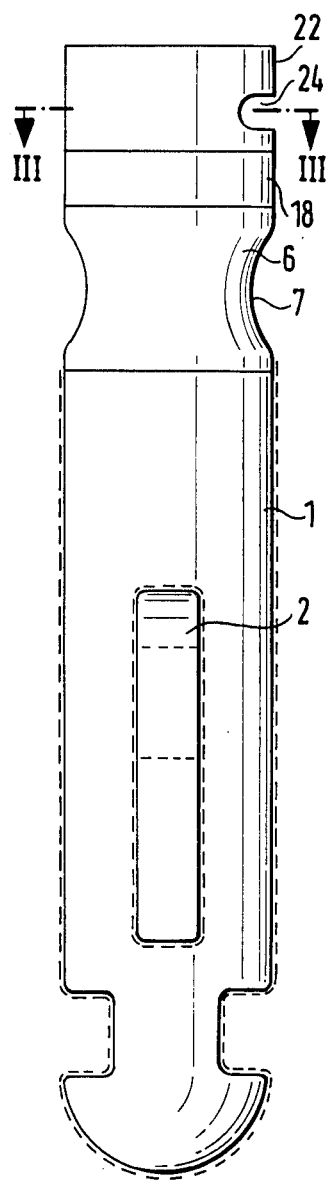
FIG. 2 is a lateral view of FIG. 1.

The implant shown in FIGS. 1 to 3 illustrates one example of the invention. It has a peg, one part of which is a tube 1 closed at is lower end and which additionally has a radial anchoring plate 2. The tube can be inserted into the jawbone with another part, insert 3, comprising a cylindrical shaft 4 which fits tightly in a bore 5 of the tube 1, and is held free from play. On its upper end, the insert 3 has a head 6 with a lateral narrow neck 7, which, in the inserted implant, lies at the level of the gums or the exit from them. The head 6 has a circumferential shoulder 8 on its lower edge which, with a tight fit, presses against the upper edge 9 of the tube 1, so that no bacteria can penetrate into the crack formed between the two.

The lower end 10 of the shaft 4 of the insert 3 terminates short of the base of the bore 5, and has a threaded stud 11 which is screwed into a corresponding threaded bore 12 in the base of tube 1. When screwed in, the long shaft 4 expands somewhat so that under stress the shaft is securely mounted.

Insert 3 has a bore 13 extending through head 6 down to the bottom 10. Mounted in bore 13 is an extension formed as a cylindrical pin 14 which interlocks with a cone 15, so that an interspace is formed above head 6, in which an intermediary sleeve 16 of resilient material, plastic, for example, is positioned. The lower side of the cone 15 forms a contact surface 17 which rests on the flange-like part 18 of the intermediary sleeve 16. The flange-like part 18 rests on the contact surface 19 comprising the upper end of the head 6. The contact surfaces 17 and 19 are curved. The surfaces of the resilient intermediary sleeve 16 and of the flange-like part 18 are cemented or cast to adjacent parts in the contact therewith.

As will be noted, especially from FIG. 1, a circular groove 20, with a radial groove 21 in the complementary inner conical fitting surface on a securing part 22, is located in the external conical surface of the frusto cone 15. An essentially U-shaped retaining clip 23 interlocks with these grooves 20 and 21, firmly connecting parts 15 and 22 with one another. A lateral slot 24 is provided in the holding part 22 for insertion of the U-shaped retaining clip 23. This connection is free from play and easily detachable. Moreover, torsion forces are transferred out of the connection so that the surrounding part of the peg is not stressed by these forces, and thus cannot loosen.

In using the implant shown in FIG. 1 to 3, a cavity is first formed in the jawbone, essentially complementary to the flanged tube 1 of the insert 3, and the tube 1 is inserted. The bore 5 is closed by a plug (not shown) which is similar to the head 6 of the insert with a very short top. The gum is closed over the plug and permitted to heal up. The gum is subsequently perforated, the plug is removed from the bore 5, and an insert 3 is firmly screwed in so that the mechanical properties of the resilient intermediary sleeve 16 and the flange-like part 18 are selected corresponding to the values of the tooth-holding mechanism of the desired limitation. In this condition, the cone 15 essentially protrudes freely so that the securing part 22 can be set on it with the tooth replacement mounted thereon. Since the holding part 22 is prefabricated with its complementary conical fitting surface, and is precisely adjusted to the conical surface of the cone 15, a highly accurate fit is provided. The holding part 22, with the tooth replacement mounted on it, is accompanied by the lateral insertion of the retaining clip 23, which can at any time be removed for inspection or cleaning and for removing the tooth replacement.

I claim:

1. An enossal implant for holding a resiliently-mounted, tight-fitting tooth replacement comprising
    a rigid metal tube insertable into the jaw bone
    a threaded bore within said tube
    a removable insert for said tube having a threaded rigid metal peg for screwing into said bore to lock the tube to the insert
    a pin disposed within said insert for mounting said tooth replacement on the outer end thereof and
    an intermediary resilient sleeve positioned between and bonded to said pin and said insert.

2. An enossal implant in accordance with claim 1, in which said intermediary sleeve is firmly connected, by cementing or casting, with said pin and said insert.

3. An enossal implant in accordance with claim 1, in which said insert has a head, said pin terminates in a cone spaced above said head, and said intermediate sleeve has a flange positioned in the space between said head and said cone.

4. An enossal implant in accordance with claim 3, in which said bore is enlarged above the threaded portion.

5. An enossal implant in accordance with claim 1, in which said peg is constructed as an expansible screw.

6. An enossal implant in accordance with claim 5, in which said insert has a cylindrical shaft tightly fitted in the bore of said tube.

7. An enossal implant in accordance with claim 6, in which said cylindrical shaft has a significantly larger diameter than said threaded peg.

8. An enossal implant in accordance with claim 3, in which said cone has a contact surface lying opposite a similar contact surface on the external end of said head, and said flange is compressed between said contact surfaces.

9. An enossal implant in accordance with claim 8, in which both the contact surfaces are curved.

10. An enossal implant in accordance with claim 8, in which the contact surface of the cone is oriented towards said pin.

11. An enossal implant in accordance with claim 3, in which said head extends in an axial direction.

12. An enossal implant in accordance with claim 11, in which said head has a circular rounded constriction on its external surface.

* * * * *